United States Patent
Steinhardt et al.

(10) Patent No.: US 8,128,694 B2
(45) Date of Patent: Mar. 6, 2012

(54) AUDITORY OSSICLE PROSTHESIS WITH VARIABLE COUPLING SURFACES

(75) Inventors: Uwe Steinhardt, Hirrlingen (DE); Heinz Kurz, Dusslingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 283 days.

(21) Appl. No.: 12/383,004

(22) Filed: Mar. 18, 2009

(65) Prior Publication Data

US 2009/0240331 A1   Sep. 24, 2009

(30) Foreign Application Priority Data

Mar. 20, 2008   (DE) .......................... 10 2008 015 114

(51) Int. Cl.
*A61F 2/18* (2006.01)
(52) U.S. Cl. ......................................................... 623/10
(58) Field of Classification Search ..................... 623/10, 623/17.17
See application file for complete search history.

(56) References Cited

U.S. PATENT DOCUMENTS

| | | | |
|---|---|---|---|
| 6,238,214 B1 * | 5/2001 | Robinson ....................... | 433/215 |
| 6,432,139 B1 * | 8/2002 | Elies et al. ...................... | 623/10 |
| 6,554,861 B2 | 4/2003 | Knox et al. | |
| 6,579,317 B2 | 6/2003 | Kurz | |
| 2002/0045939 A1 | 4/2002 | Kurz | |
| 2004/0162614 A1 | 8/2004 | Steinhardt et al. | |
| 2004/0204759 A1 * | 10/2004 | Blom et al. .................... | 623/9 |
| 2006/0271190 A1 | 11/2006 | Reitan et al. | |
| 2007/0021833 A1 | 1/2007 | aWengen et al. | |

(Continued)

FOREIGN PATENT DOCUMENTS

DE   1926587 A1   7/1970

(Continued)

OTHER PUBLICATIONS

U.S. Appl. No. 12/383,005, Applicant: Uwe Steinhardt et al., filed Mar. 18, 2009 entitled Auditory Ossicle Prosthesis with variable coupling surfaces.

(Continued)

*Primary Examiner* — Thomas J Sweet
*Assistant Examiner* — Seema Swaminathan
(74) *Attorney, Agent, or Firm* — Flynn, Thiel, Boutell & Tanis, P.C.

(57) ABSTRACT

An auditory ossicle prosthesis (10) which comprises, at one end, a plate-shaped first securing element (11) for bearing on the tympanic membrane or on the footplate of the stirrup, and, at its other end, a second securing element (12) for mechanical connection to the ossicular chain or to the inner ear, and also a connection element (13) that connects the two securing elements so as to conduct sound, wherein the first securing element has a radially inner coupling area (14) for coupling the first securing element to the connection element, and also a plurality of web elements (15, 15', 15") for radial connection of the coupling area to radially outer portions (16, 16', 16") of the first securing element, is characterized in that the web elements are of such a geometric configuration, and their material so chosen, that the web elements can be easily broken off and the radially outer portions appended to them detached from the first securing element, such that the external diameter of the first securing element is reduced in this area. This means that the number of different prostheses to be kept ready during an operation can be reduced to a single standard prosthesis, without losing the possibility of optimal adaptation of the prosthesis to the specific case of use.

22 Claims, 8 Drawing Sheets

U.S. PATENT DOCUMENTS

| | | | |
|---|---|---|---|
| 2007/0083263 A1 * | 4/2007 | Steinhardt et al. | 623/10 |
| 2008/0234817 A1 | 9/2008 | Huettenbrink et al. | |
| 2009/0164010 A1 | 6/2009 | Steinhardt et al. | |

FOREIGN PATENT DOCUMENTS

| | | | |
|---|---|---|---|
| DE | 19744789 A1 | | 4/1998 |
| DE | 29802776 U1 | | 4/1998 |
| DE | 19647579 A1 | * | 5/1998 |
| DE | 299 04 770 U1 | | 7/1999 |
| DE | 10 2007 013 708 B3 | | 1/2008 |
| DE | 20 2007 012 217 U1 | | 1/2008 |
| DE | 10-2007-062 151 B3 | | 12/2008 |
| EP | 1 181 907 B1 | | 2/2002 |
| WO | WO 02/069850 A1 | | 9/2002 |

OTHER PUBLICATIONS

U.S. Appl. No. 12/383,004, Applicant: Uwe Steinhardt et al., filed Mar. 18, 2009 entitled Auditory Ossicle Prosthesis with variable coupling surfaces.

Yung, M.W., Brewis, C., "A comparison of the user-friendliness of hydroxyapatite and titanium ossicular prostheses", *The Journal of Laryngology & Otology*, Feb. 2002, vol. 116, pp. 97-102.

European Patent Office Search Report dated Jun. 17, 2009 for European Application No. 09 00 3942 (3 pages).

* cited by examiner

AUDITORY OSSICLE PROSTHESIS WITH VARIABLE COUPLING SURFACES

BACKGROUND OF THE INVENTION

The invention relates to an auditory ossicle prosthesis which replaces or spans at least one member or parts of one member of the ossicular chain, wherein the auditory ossicle prosthesis comprises, at one end, a substantially plate-shaped first securing element for bearing on the tympanic membrane or on the footplate of the stirrup, and, at its other end, a second securing element for mechanical connection to a member or parts of a member of the ossicular chain or to the inner ear, and also a connection element that connects the two securing elements to each other so as to conduct sound, and wherein the plate-shaped first securing element has a radially inner coupling area, arranged centrally especially around the area centroid of the plate-shaped first securing element, for mechanically coupling the first securing element to the connection element, and also a plurality of web elements for radial connection of the radially inner coupling area to radially outer portions of the first securing element, wherein the web elements are of such a geometric configuration, and their material so chosen, that the web elements can be broken off from the plate-shaped first securing element and the radially outer portions appended to them detached from the first securing element.

A device of this kind is known from DE 10 2007 013 708 B3.

Auditory ossicle prostheses are used to transmit sound or a sound signal from the tympanic membrane to the inner ear when the ossicles of the human middle ear are entirely or partially absent or damaged. The auditory ossicle prosthesis has two ends, and, depending on the specific circumstances, one end of the auditory ossicle prosthesis is secured to the tympanic membrane, for example by means of a headplate, and the other end of the auditory ossicle prosthesis is secured, for example, to the stirrup of the human ossicular chain or plunged directly into the inner ear. With the known auditory ossicle prostheses, the sound conduction or signal transmission between the tympanic membrane and the inner ear is often made possible only to a limited extent, since these prostheses are able only to an extremely limited extent to replace the natural anatomical features of the ossicular chain.

After the prosthesis has been placed surgically in the middle ear and the tympanic membrane has been closed again, the so-called incorporation phase starts. During this period, scars and tissue strands form and generate unpredictable forces, which can lead to the prosthesis shifting from its local position. In the case of a stiff connection between headplate and shaft, increased pressure peaks can occur between the edge of the headplate and the tympanic membrane or the transplant between tympanic membrane and headplate. These pressure peaks can be so high as to result in penetration or extrusion through the tympanic membrane. For this reason, it is very useful if, after the operation, the prosthesis has a certain degree of mobility and flexibility, such that the headplate is able to automatically adapt itself to the position of the tympanic membrane after the operation.

Since the anatomical features of the ear, for example the position, shape and size of the stirrup, anvil, hammer and tympanic membrane, also vary between individuals, it is very advantageous if auditory ossicle prostheses are not made rigid, but instead have a certain flexibility or variability.

To achieve this flexibility or variability, various securing and coupling devices for auditory ossicles are known that have elastic parts and/or hinges. Such a hinged connection between a securing element, mounted on the footplate of the stirrup, and the elongate shaft is described in EP 1 181 907 B1 and is offered by the Applicant under the brand name "Ball-Joint".

Another complication that occurs occasionally is the result of insufficient air in the middle ear cavity and of associated acute or chronic inflammations, tumor formations, adhesions in the region of the tympanic membrane and stiffening of the latter. In cases of dysfunction of the Eustachian tube, for example, an underpressure may develop in the middle ear and cause eversion or so-called retraction of the tympanic membrane, with resulting adhesion to the stirrup, for example. To counteract this and to be able to follow the postoperative movements of the tympanic membrane, the headplates in known auditory ossicle prostheses are designed to be able to tilt relative to the connection element that connects the headplate to the second securing element and that is in most cases designed as an elongate shaft. A headplate of this kind, which is inherently rigid but is able to tilt relative to the connection element, is described inter alia in US 2004/0162614 A1, in the article by M. W. Yung, Ph.D, F.R.C.S, D.L.O. and C. Brewis, F.R.C.S. entitled "A comparison of the user-friendliness of hydroxyapatite and titanium ossicular prostheses" in the Journal of Laryngology & Otology, February 2002, volume 116, pages 97-102, or, for example, also in US 2006/0271190 A1.

However, a disadvantage of these known auditory ossicle prostheses is that, in the event of local medial movements of the tympanic membrane, the inherently rigid tilting of the headplate means that the opposite side of the headplate is also moved out laterally at the same time, as a result of which pressure peaks are generated on the tympanic membrane.

In order to achieve a high level of postoperative flexibility and variability of the prosthesis, while at the same time considerably improving the quality of the sound conduction through the prosthesis, without causing the above-mentioned complications to occur, the aforementioned document DE 10 2007 013 708 B3 proposes that the web elements are of such a geometric configuration that, in the event of local medial movement of the tympanic membrane, they are able to follow this medial movement locally, but do not transmit the movement to remote areas of the headplate. In the event of a slight medial movement of the tympanic membrane, this flexible configuration of the auditory ossicle prosthesis avoids rigid tilting of the whole headplate. Instead, the headplate twists upon itself locally but, in the event of movements of the tympanic membrane caused by sound, it nevertheless transmits these movements to the connection element, such that an optimal transmission of the sound or of the sound signal from the tympanic membrane to the middle ear and onward to the inner ear is ensured.

This provides a very considerable improvement over the rest of the known prior art. Unfortunately, however, further problems still persist that cannot be solved by these measures alone:

In the context of a tympanoplasty procedure in the human middle ear, the pathology and anatomy may necessitate very different kinds of structural reconstructions that are specific to each individual patient. Depending on the extent and shape of any parts of the middle ear anatomy that are still present and that are perhaps partially intact, for example the hammer (malleus), the anvil (incus), the stirrup (stapes) or the tympanic membrane, the middle ear prostheses to be implanted need to have a correspondingly large number of different geometries, some of them differing quite considerably in shape and size.

Since, before the start of surgery of the middle ear, it cannot be predicted, or can be predicted only with great difficulty (only roughly if at all, and practically never exactly), how the subsequent reconstruction of the tympanic membrane and of the ossicular chain will turn out in the course of the operation, a very large number of middle ear prostheses with different geometries, shapes and sizes have to be kept ready for each operation that is to be performed, so as to ensure that the surgeon can at all times select the most suitable prosthesis during the operation, that is to say the prosthesis allowing him to deal with the specific case in question. Otherwise, it may not be possible to guarantee optimal treatment.

Another factor is that said problems of adapting the auditory ossicle prosthesis during surgery may occur not only in the area where the first securing element bears on the tympanic membrane, but also in the area of a likewise plate-shaped second securing element which may be required to allow the prosthesis to bear on the footplate of the stirrup. Particularly for the area of a total reconstruction toward the inner ear, a total prosthesis for this purpose normally has a stamp with a standard diameter of 0.8 mm. Surgeons often express the wish that different surface areas could be made available, depending on the intraoperative situation, to be placed onto the footplate of the stirrup. This desire among specialists would be satisfied by provision of an additional securing element which is connected or can be connected to the stamp and which, in terms of the size of its surface, would be able to be varied within wide limits.

If the auditory ossicle prosthesis is not a total prosthesis, and the first securing element is therefore not designed as a headplate for bearing on the tympanic membrane, but instead as a clip for securing the prosthesis on a member of the ossicular chain, the described problems of adaptation occur exclusively at the inner ear end of the auditory ossicle prosthesis.

A further problem is that, throughout the world, extremely different surgical techniques are employed, which postulate different types of reconstructions in the middle ear. These require suitably adapted middle ear prostheses which differ greatly from one another in size and shape and which again have to be kept ready during each operation in order to allow the surgeon to employ what he considers to be the best method in each particular case.

SUMMARY OF THE INVENTION

In light of this, the object of the present invention is to improve a middle ear prosthesis of the type described above by the simplest possible technical means and at minimal cost, such that the number of different prostheses to be kept ready during an operation can be considerably reduced, preferably to a single standard prosthesis, without in so doing losing the possibility of optimal adaptation of the prosthesis in each particular case.

According to the invention, this object is achieved in a surprisingly simple and effective way, by virtue of the fact that the web elements each have a predetermined break point of minimum width. In this way, when a radially outer portion is broken off, the web element breaks off at a defined location, and the external diameter of the first securing element is reduced in this area.

The plate-shaped first securing element of the middle ear prosthesis according to the invention can be designed, for example, as a headplate placed against the tympanic membrane in the context of a tympanoplasty procedure and is constructed such that it is variable within very wide limits in terms of its shape and surface. During surgery, the prosthesis according to the invention, kept ready as a standard prosthesis, can thus be reconfigured very easily, very flexibly and in an extremely targeted manner that meets the situation particular to a specific patient.

Simple ad hoc changes can be made to the standard prosthesis according to the invention, for example to the angles, lengths or surface areas, to serve the purpose of greatly improved adaptation to each particular case. Thus, the middle ear prosthesis according to the invention affords the operating surgeon an extremely high degree of variation and flexibility, without the previous requirement to keep in stock a large number of very different prosthesis shapes, sizes and geometries. It is thus possible for the surgeon, during the operation, to make specific changes to the prosthesis that allow him to adapt or adjust the prosthesis specifically to the particular set of circumstances.

With the technique used according to the invention, it is quite simple to change, for example, the size of the headplate of the prosthesis by simply breaking off radially outer portions that are not needed, such that it touches only very specific areas of the tympanic membrane—generally those that are known to play an essential role in acoustic transmission.

It often happens that the manubrium is present on the tympanic membrane, or indeed that it is missing, depending on how many previous operations have been performed, which operating method was employed and which specific measure was taken. Accordingly, a headplate configured according to the invention with a variable surface allows the operating surgeon to react precisely and correctly, i.e. allows the area responsible for the manubrium to be detached or, if need be, left on the headplate.

A similar situation also applies to the coupling of the auditory ossicle prosthesis to the footplate of the stirrup, where likewise on account of the inventively surface-variable design of the corresponding plate-shaped securing element, a hitherto unknown intraoperative flexibility in terms of optimal adaptation to the situation presented by the individual patient can be offered.

Generally, by means of the present invention, more specific adaptation to the individual anatomy of the patient can be achieved by simply breaking off parts of a tympanic membrane headplate or of a stirrup footplate, this kind of adaptation previously having been possible only by using middle ear prostheses that were very complicated and expensive and produced by hand, and with which in most cases a further operation was required, because the exact dimensions can generally be established only after the middle ear space has first been opened.

The basic concept according to the invention can be doubly exploited if both securing elements are plate-shaped with breakable web elements and with radially outer portions appended thereto, wherein the first securing element is designed to allow the auditory ossicle prosthesis to bear on the stirrup footplate, and the second securing element serves as a flat headplate for mechanical connection to the tympanic membrane.

It is also expedient if the plate-shaped first securing element (and, if appropriate, also the second securing element) of the auditory ossicle prosthesis according to the invention has a thickness, in particular a plate thickness t, of between 0.01 mm and 0.5 mm, preferably between 0.1 mm and 0.25 mm, and a minimum diameter D of between 1.5 mm and 8 mm, preferably between 2 mm and 5 mm, and the web elements have a maximum width b of between 0.01 mm and 0.3 mm, preferably between 0.05 mm and 0.2 mm.

In one class of advantageous embodiments of the auditory ossicle prosthesis according to the invention, web elements, starting from the central coupling area, extend radially outward in a star shape, with a respective radial outer portion being appended to each of them, and further radially outer portions being appended to each of these radially outer portions via further web elements. A large number of radially outer portions of the first securing element are made available in this way. By breaking off individual portions or whole groups of these portions in a deliberate way, almost any desired geometry of the securing element can now be very easily produced ad hoc without using additional aids.

In an alternative class of embodiments, the radially outer portions of the plate-shaped first securing element form an outer ring area which, because of its high geometrical moment of inertia, considerably increases the stability of the securing element.

One group of developments of these embodiments is characterized in that the radially outer ring area is uninterrupted and closed. In this way, the stability of the first securing element is further increased. If said element is designed as a headplate, it is also possible, in the case of postoperative retractions, to avoid the formation of dangerous points directed at the tympanic membrane.

As an alternative to this, in another group of developments, the radially outer ring area has at least one interruption, preferably several interruptions. In this way, in particular, asymmetrical shapes can be easily produced. In addition, a plastic deformation of the plate-shaped first securing element is made easier by stretching or pressing together the ring area, divided into portions, within the plate plane, and this opens up further possibilities of shaping.

In developments of the embodiments described above, the radially outer ring area can have an oval or circular shape, which is known per se from the prior art and easy to produce. This will generally constitute the standard version of the auditory ossicle prosthesis according to the invention.

To make the auditory ossicle prosthesis easier to implant surgically, in a special variant the radially outer ring area can have a unilateral recess for receiving the manubrium.

In another variant, the radially outer ring area of the plate-shaped first securing element has a bulge that extends radially outward in the plane of the plate and that is able to engage in structures of the ossicular chain.

However, a variant is also possible in which the radially outer ring area has an undulating outer contour, which may prove favorable in specific geometric situations in the middle ear, of the kind that may often be found in practice in the patient.

It is particularly expedient if the web elements have a maximum width b and the radially outer ring area has a maximum width B, where b<B, preferably 2b<B.

In order to achieve a desired flexibility in the case of a maximum width b of the web elements and a minimum diameter D of the plate-shaped first securing element, including the optionally present ring area, the following should apply: $b \leqq 0.05$ D, preferably $b \approx 0.03$ D. In the prior art, for example in the auditory ossicle prostheses described in US 2004/0162614 A1, the ratio b/D is at least 0.1 or above.

It is also expedient if the plate-shaped first securing element of the auditory ossicle prosthesis according to the invention has a thickness, in particular a plate thickness t of between 0.01 mm and 0.5 mm, preferably of between 0.1 mm and 0.25 mm, and a minimum diameter D of between 1.5 mm and 8 mm, preferably of between 2 m and 5 mm, and the web elements have a maximum width b of between 0.01 mm and 0.3 mm, preferably of between 0.05 mm and 0.2 mm.

In order to avoid injuries, the break-off area of the breakable web elements should be configured such that no sharp ridge formed by the outermost edge after breaking comes into direct contact with the tympanic membrane or other contiguous structures. For this reason, embodiments of the auditory ossicle prosthesis according to the invention are particularly preferred in which the web elements each open into a recess of the central coupling area and/or of one of the radially outer portions, which recess encloses the sharp ridge, almost always caused by the break, and as it were screens this sharp ridge off from the outside.

In practice, developments of these embodiments have proven useful in which the recess, in the plane of the plate-shaped first securing element, radially encloses the corresponding web element to such an extent that the web element extends along at least ¼, preferably at least ⅓, of its length within the recess.

A particularly advantageous development of these embodiments is characterized in that the predetermined break point, in the plane of the plate-shaped first securing element, is arranged within a recess, which then conceals the break-off edge and also the sharp ridge that occurs when the web element is broken off.

A class of embodiments of the invention is also preferred in which at least one extension piece is provided which, like a jigsaw piece, can be joined from the side onto the outer edge of the plate-shaped first securing element in the plate plane. This opens up a huge number of design possibilities in terms of the geometric shape of the securing element.

In particular, it is now no longer essential to implant symmetrical shapes, as were required hitherto with the available standard prostheses. Instead, the operating surgeon is easily able, during the operation, to produce by hand an optimally adapted auditory ossicle prosthesis that is tailor-made to the situation.

It often happens that the manubrium is present on the tympanic membrane, or indeed that it is missing, depending on how many previous operations have been performed, which operating method was employed and which specific measure was taken. Accordingly, a headplate configured according to the invention with a variable surface allows the operating surgeon to react precisely and correctly, i.e. allows the area responsible for the manubrium to be detached or, if need be, joined. In advantageous developments of this class of embodiments, the extension piece that can be joined on from the side is then shaped as an appendix for the hammer or the manubrium of the auditory ossicle prosthesis and, in the state when joined together, protrudes radially outward from the edge of the plate-shaped first securing element.

These developments can be further improved by the fact that the extension piece that can be joined on from the side is anchored resiliently in the first securing element, which in particular makes inadvertent breaking-off of the very fine miniature part upon joining to the securing element very difficult.

The resilient anchoring of the extension piece can be achieved by means of a simple clip element, for example.

In other advantageous variants, the extension piece that can be joined on from the side is anchored in the first securing element with a snap-fit action and thus secure against loss, particularly by means of barbs.

In the auditory ossicle prosthesis according to the invention, the connection element between the securing elements is generally designed as an elongate shaft, as is well known per se from the prior art.

In order to increase the above-mentioned flexibility and variation of the prosthesis, as is described per se in EP 1 181

907 B1, it is possible, in a particularly preferred development of this embodiment, to provide at least one ball joint on or in the elongate shaft. Variants in which the elongate shaft comprises a large number of further rotation elements adjoining one another, preferably as a ball joint chain, are advantageous in terms of a high degree of postoperative mobility of the prosthesis.

Alternatively, however, in particularly simple and inexpensive embodiments of the prosthesis according to the invention, the shaft can also be made in one piece and be particularly rigid.

Depending on the individual defect that is to be remedied in a patient by use of the auditory ossicle prosthesis according to the invention, or that is at least to be alleviated in terms of its effects, the construction of the prosthesis is designed accordingly. In many embodiments of the invention used in practice, the first securing element will comprise a headplate designed to bear on the tympanic membrane. In many other embodiments, for example, the prosthesis can be secured at one end to the process of the anvil and at the other to the stirrup, or it can be plunged directly into the inner ear. In this connection, an advantageous design is one in which the auditory ossicle prosthesis is located at the end point of the hammer (umbo) or directly next to it, as a result of which the maximum lever action is achieved for mechanically transmitting sound through movements in the artificial or natural ossicular chain.

One class of embodiments of the auditory ossicle prosthesis according to the invention is distinguished by the fact that the second securing element is formed as a plate, as a sleeve, as a loop, as a closed bell, as a singly or multiply slit bell or as a clip for mechanical connection to a further member of the ossicular chain.

In developments of these embodiments, the prosthesis is secured on the one hand to the tympanic membrane by way of the first securing element designed as headplate and on the other hand to the anvil or to the stirrup by way of the second securing element.

In alternative embodiments, provision may be made that the auditory ossicle prosthesis is at one end coupled directly to the inner ear, in particular via a plunger, by means of perforation of the footplate of the stirrup (stapedectomy or stapedotomy) and/or by means of opening the human cochlea (cochleotomy).

Embodiments of the invention are possible in which the prosthesis or parts thereof is/are made of biocompatible plastics, in particular silicone, polytetrafluoroethylene (PTFE) or polyether ether ketone (PEEK) and/or composite fiber materials, in particular carbon fibers. Post-operative rejection reactions can in most cases be avoided using these materials.

The auditory ossicle prosthesis according to the invention or parts thereof can be made of titanium and/or of gold and/or of tantalum and/or of steel and/or of an alloy of said metals. In addition to its strength and excellent sound conduction properties, the material titanium in particular also has excellent biocompatibility in the middle ear in humans.

In view of the above-mentioned post-operative adjustment of position, embodiments of the invention are advantageous in which the prosthesis or parts thereof, in particular one of the securing elements, is made of a material with shape memory or with superelastic properties, preferably nitinol, which is known per se from, for example, WO 02/069850 A1 or U.S. Pat. No. 6,554,861 B2.

In further embodiments, parts of the auditory ossicle prosthesis can alternatively or additionally be made from a ceramic material.

In addition to the post-operative change of position, a further problem also arises after implantation of auditory ossicle prostheses. This is due to the fact that the middle ear of the human body constitutes a "semi-open bearing". Any implantation material introduced into the body, in the context of a reconstruction of the middle ear and of its structures, is therefore subject to a particular stress arising from the fact that it lies in a contaminated and infected environment, which generally attacks the material. Since the aim of implanting an auditory ossicle prosthesis must be that the implant remains in the patient's middle ear for as long as possible and without complications, a protracted attack of the material can lead to damage of the prosthesis and/or to local infection. Both consequences are unacceptable. To prevent damage of the implanted material and also of the surrounding tissue on a permanent basis, another particularly preferred embodiment of the invention involves a biologically active coating, in particular a coating that inhibits growth and/or promotes growth and/or has an antibacterial action, being provided at least in some areas of the surface of the auditory ossicle prosthesis.

In the auditory ossicle prosthesis according to the invention, a securing element designed as headplate should in principle have a coating that promotes growth, whereas a securing element leading directly into the ear, and designed in the form of a plunger for example, should have a coating that inhibits growth.

An embodiment of the auditory ossicle prosthesis according to the invention is particularly preferred in which the weight distribution of the individual parts of the prosthesis is calculated as a function of a desired, predefined or predefinable frequency response of the sound conduction in the middle ear. It is thus possible, without major additional technical outlay, to achieve a degree of mechanical tuning of the sound propagation properties by means of an individually configured auditory ossicle prosthesis.

Such a tuning effect can be achieved, in particular embodiments, by the fact that at least one additional weight is secured on a part of the ossicular chain or of the prosthesis as a function of a desired, predefinable frequency response of the sound conduction in the middle ear. In advantageous developments of these embodiments, the additional weight is secured on a part of the ossicular chain or the prosthesis by means of a clip. In addition, the additional weight and/or the clip can also be coated with a biologically active coating.

A further embodiment of the invention, finally, is distinguished by the fact that the prosthesis is connected to an active vibration part of an active, in particular implantable hearing aid. In this way, extensive hearing damage can also be largely remedied by application of modern electronics or can at least be substantially alleviated in terms of its effects, in which case, on account of the above-described coating, a physical connection of the prosthesis to the outside world does not cause any problems resulting from increased bacterial ingress into the area of the middle ear, if the coating is made suitably antibacterial.

Further features and advantages of the invention will become clear from the following detailed description of illustrative embodiments of the invention, from the figures in the drawing, which shows important details of the invention, and also from the claims. The individual features can each be realized singly or in any desired combinations in variants of the invention.

Illustrative embodiments of the invention are depicted in the schematic drawing and are explained in more detail in the following description.

BRIEF DESCRIPTION OF THE DRAWINGS

FIGS. 1a-b show an embodiment of the auditory ossicle prosthesis according to the invention with a first securing element which has a star-shaped structure and is designed as a tympanic membrane headplate, with a ball joint in the connection element, and with a second securing element shaped like a plunger;

FIGS. 2a-b show an embodiment with two plate-shaped securing elements;

FIGS. 3a-b show an embodiment with an extension piece which is shaped as an appendix for the hammer or the manubrium on the first securing element, and with a clip-shaped second securing element;

DESCRIPTION OF THE PREFERRED EMBODIMENTS

Figure 1A:
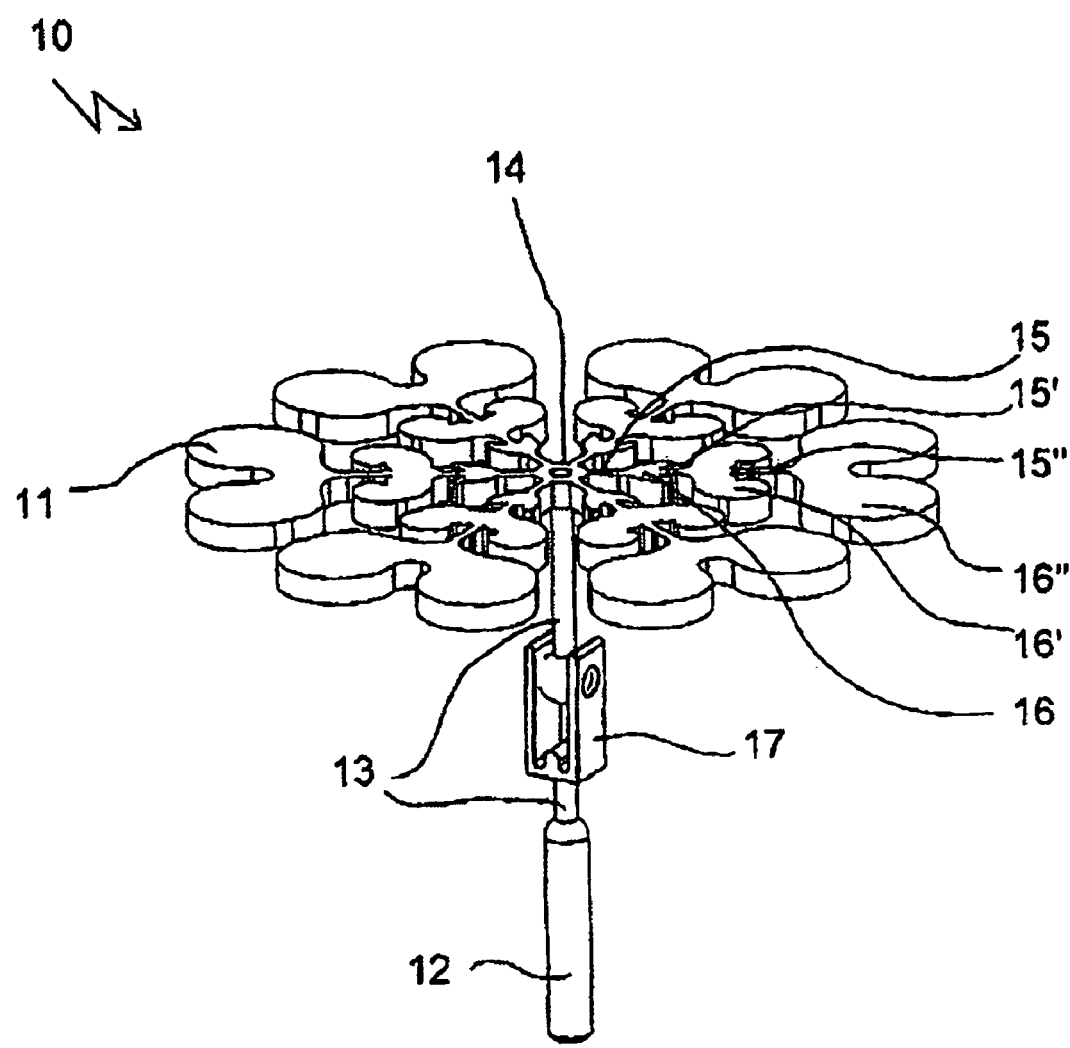
FIGS. 1*a-b*, 2*a-b* and 3*a-b* of the drawing are divided into groups of two, the respective individual figures of a group being distinguished from one another by a number followed by a, b. The "a" figures in each case show a schematic perspective view of an embodiment of the auditory ossicle prosthesis according to the invention, while the "b" figures show in detail the first securing element designed according to the invention and belonging to the corresponding "a" figure. Moreover, elements having the same structure and/or the same function are identified by the same reference number in the drawing.

The auditory ossicle prostheses 10; 20; 30; 40 according to the invention each have, at one end, a plate-shaped first securing element 11; 21; 31 which is designed in the form of a headplate for bearing on the tympanic membrane or as a footplate for bearing on the footplate of the stirrup. At the other end of the auditory ossicle prostheses 10; 20; 30; 40, there is a second securing element 12; 22; 32; 42 for mechanical connection of the prosthesis to a member or parts of a member of the ossicular chain or directly to the inner ear. Arranged between these is a connection element 13; 23; 33 which connects the two securing elements to each other so as to conduct sound and which, in the embodiments shown, is designed in the form of a one-part or multi-part, short or long shaft.

The plate-shaped first securing element 11; 21; 31 in each case has a radially inner coupling area 14; 24; 34; 54, arranged around its area centroid, for mechanically coupling the first securing element 11; 21; 31 to the connection element 13; 23; 33, and also a plurality of web elements 15, 15', 15"; 25, 25'; 35, 35', 35"; 55 for radial connection of the radially inner coupling area to radially outer portions 16, 16', 16"; 26, 26'; 36, 36', 36"; 56 of the first securing element 11; 21; 31.

The web elements 15, 15', 15"; 25, 25'; 35, 35', 35"; 55 are of such a geometric configuration, and their material so chosen, that the web elements 15, 15', 15"; 25, 25'; 35, 35', 35"; 55 can be easily broken off from the plate-shaped first securing element 11; 21; 31 and the radially outer portions 16, 16', 16"; 26, 26'; 36, 36', 36"; 56 appended to them detached from the first securing element 11; 21; 31, such that the external diameter of the first securing element 11; 21; 31 is reduced in this area.

Figure 1B:
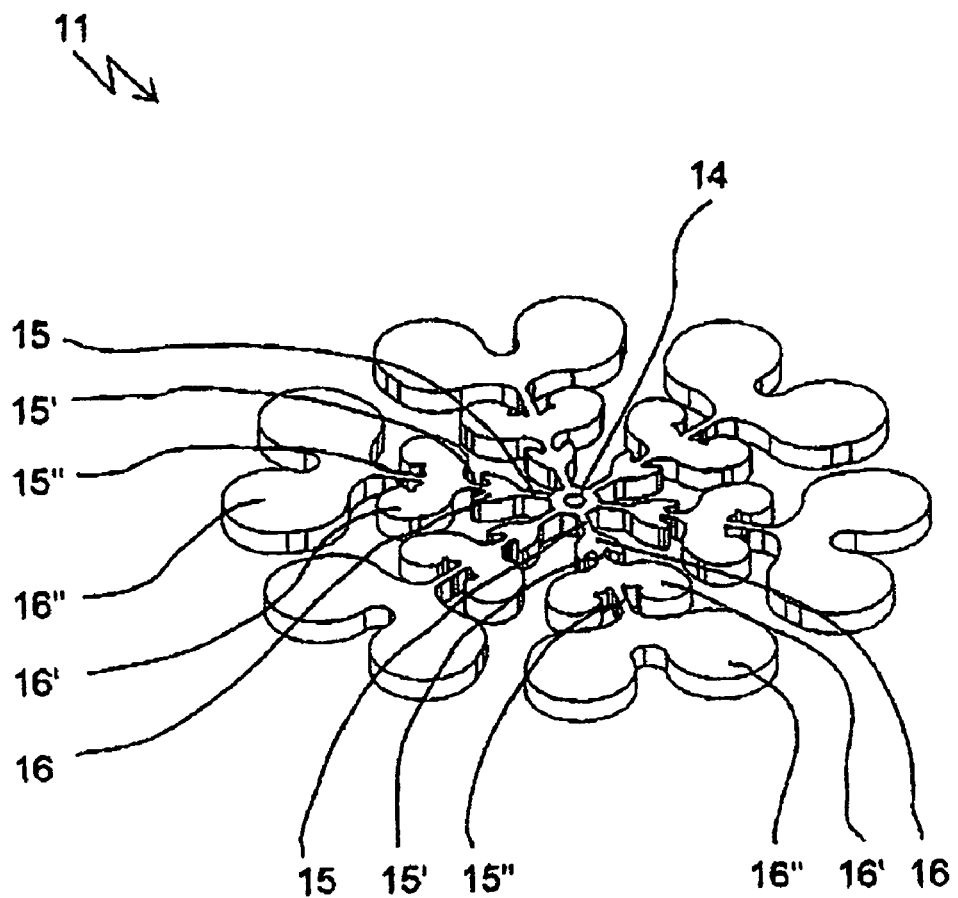

The embodiment shown in FIGS. 1a-b has, as first securing element 11, a headplate, and, as connection element 13, a two-part shaft which, between its two parts, comprises a ball joint 17 for increasing the mechanical flexibility of the shaft. The second securing element 12, at the end remote from the headplate in the auditory ossicle prosthesis 10 according to FIG. 1a, is designed in the present illustrative embodiment as a plunger for directly coupling the auditory ossicle prosthesis 10 to the inner ear.

The first securing element 11 is constructed in such a way that, starting from the central coupling area 14, web elements 15 extend radially outward in a star shape, with a respective radially outer portion 16 being appended to each of them, and that further radially outer portions 16', 16" are appended to each of these radially outer portions 16 via further web elements 15', 15".

Figure 2A:
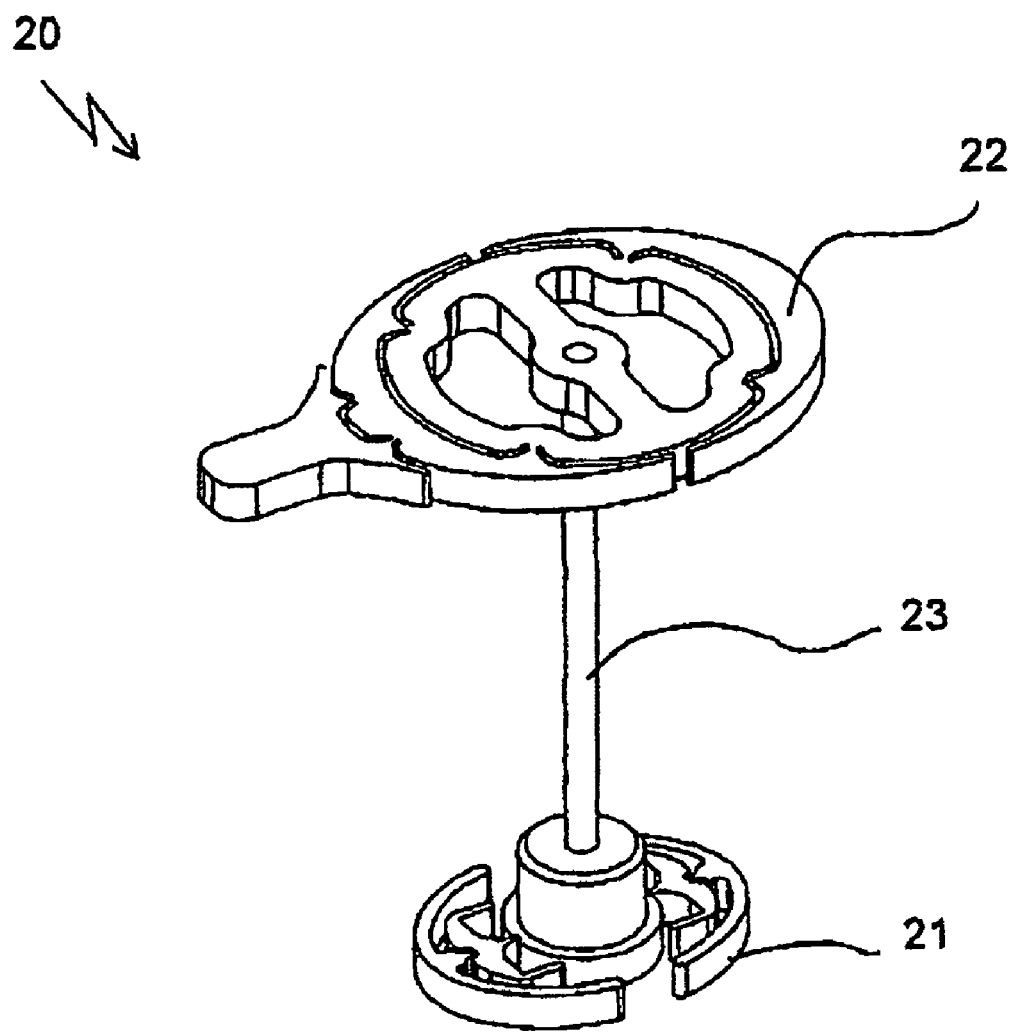
Figure 2B:
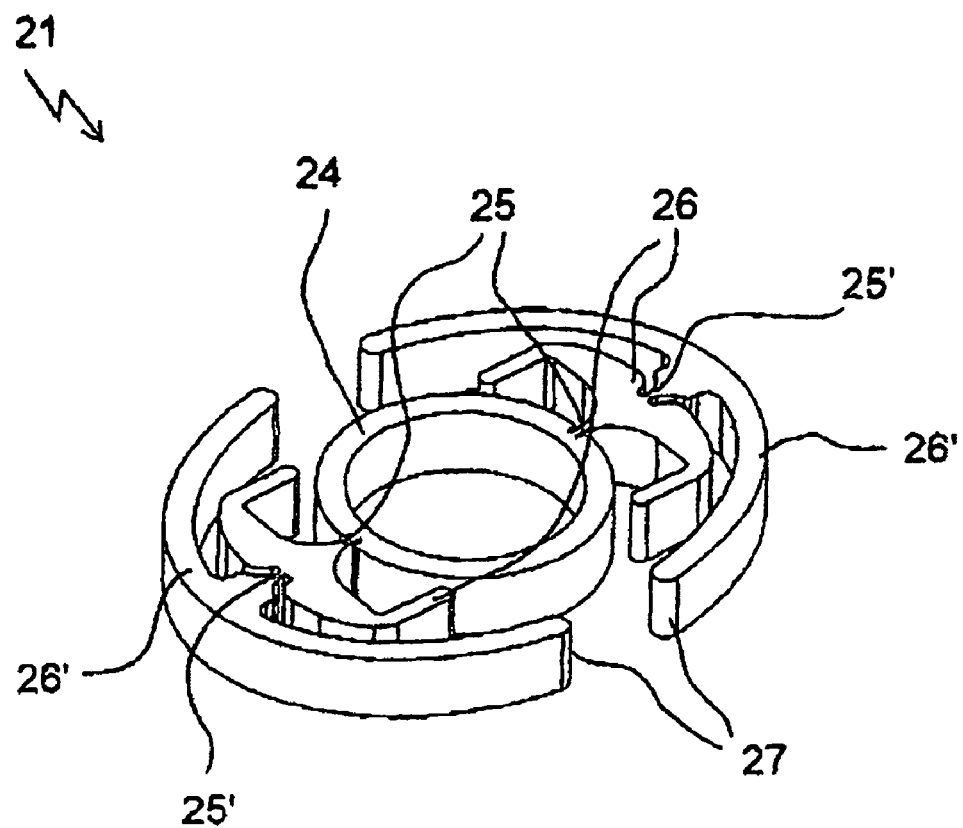

In the embodiment according to FIGS. 2a-b, the two securing elements 21, 22 have a plate-shaped configuration and, according to the invention, their web elements 25, 25' can again be easily broken off, wherein the first securing element 21 is designed to allow the auditory ossicle prosthesis 20 to bear on the footplate of the stirrup, while the second securing element 22 serves as a flat headplate for mechanical connection to the tympanic membrane. The second securing element 22 is also identical to the first securing element 31 shown in FIG. 3b.

Since this constitutes a total prosthesis, the connection element 23 is designed as a long rigid shaft formed continuously in one piece. In the first securing element 21 also, a radially inner coupling area 24 is connected via several web elements 25, 25' to radially outer portions 26, 26' that surround the coupling area 24, wherein the radially inner coupling area 24 is also in this case designed as a ring area, but with a greater internal free diameter than in the embodiment according to FIG. 1b. As is shown in FIG. 2a, the coupling area 24 can therefore be easily clamped onto a plunger-shaped thickening of the connection element 23 at its end remote from the second securing element 22.

Figure 3A:
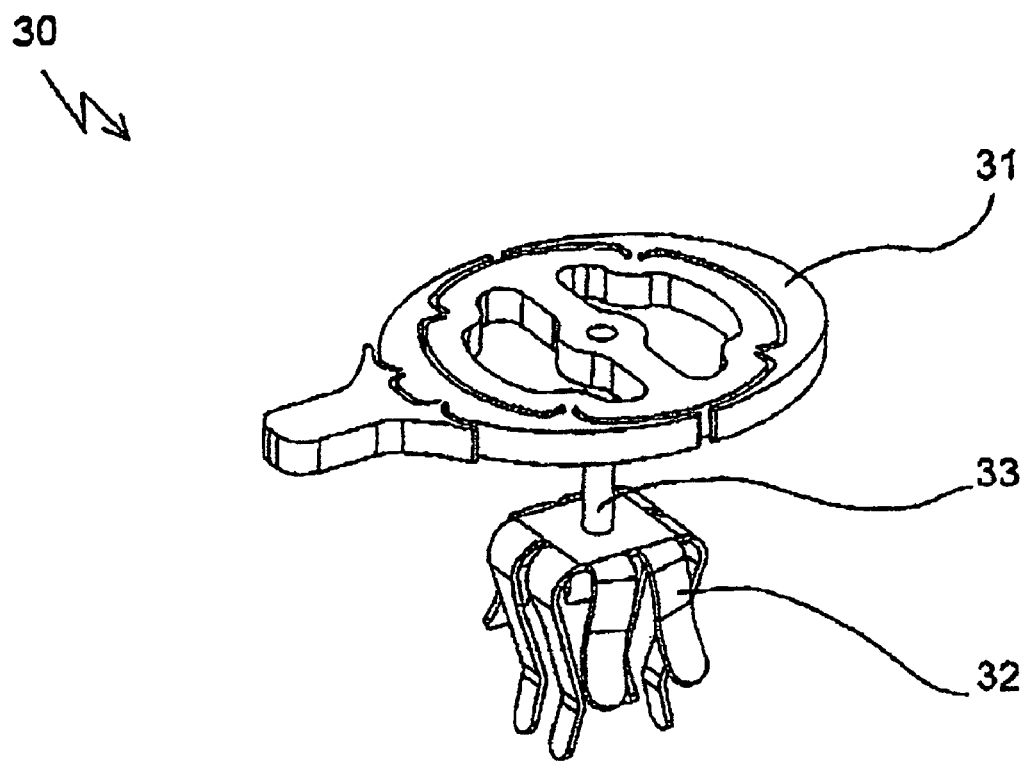
Figure 3B:
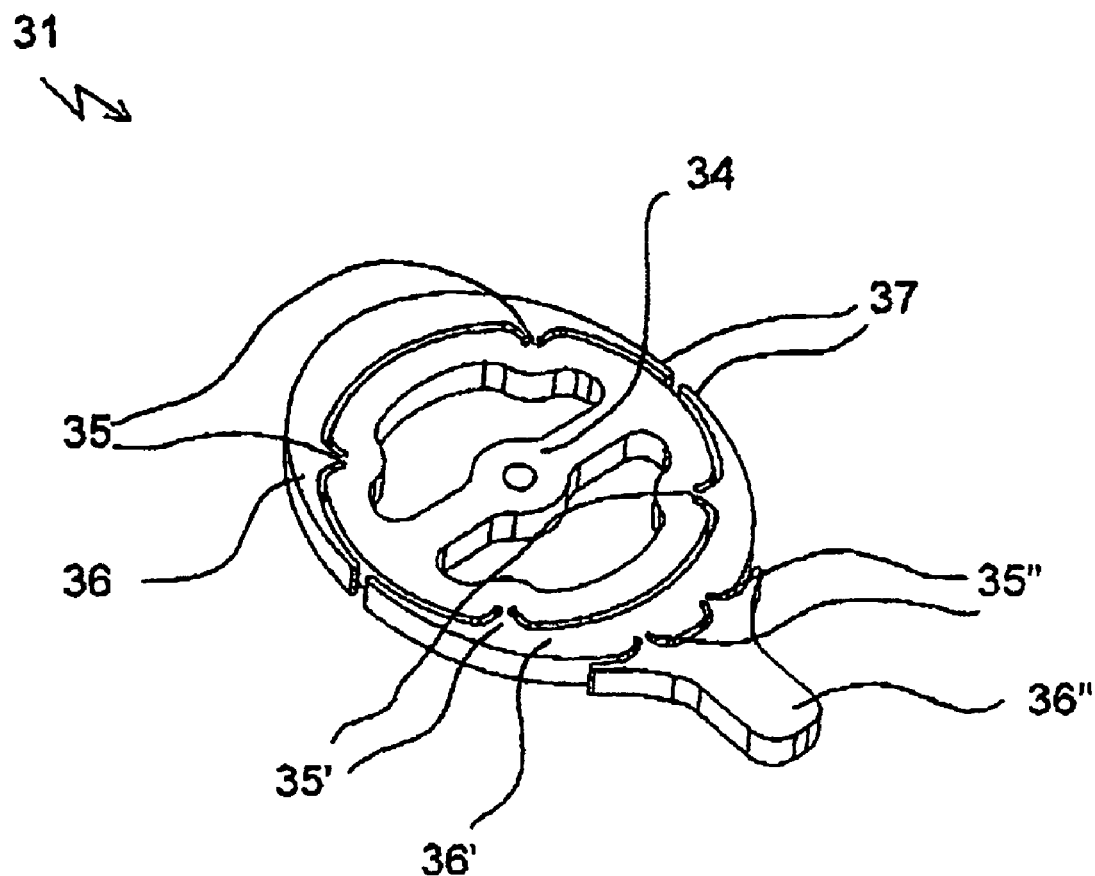
Figure 4:
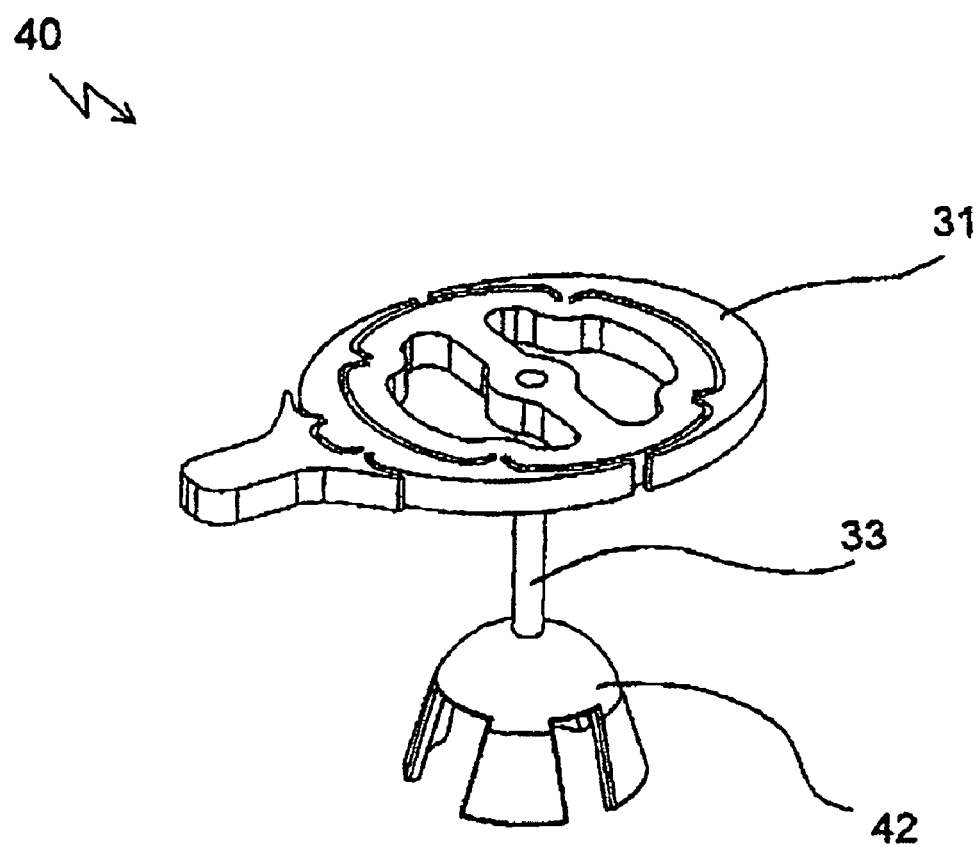
FIG. 4 shows an embodiment with a first securing element as in FIG. 3a, and with a slotted bell as second securing element.

In the illustrative embodiment shown in FIGS. 2a-b and also in the embodiments according to FIGS. 3a-b and 4, radially outer portions 26, 26' and 36, 36' surround the radially inner coupling area 24; 34, respectively, in the form of an outer ring area 27; 37 with interruptions in the azimuthal plane.

The embodiments in FIGS. 3a-b and 4 are further distinguished by the fact that the first securing element 31 in each case comprises a portion 36" which is designed as an extension piece and which, at the outer edge of the plate-shaped first securing element 31, protrudes laterally outward from the radially outer portion 36' in the plane of the plate. In the embodiments shown in the drawing, this lateral extension piece 36" is designed as a lug-shaped appendix for the hammer or the manubrium of the auditory ossicle prostheses 30; 40.

The second securing element 32 in the auditory ossicle prosthesis 30 according to FIG. 3a is designed as a clip with several tongues, whereas in the auditory ossicle prosthesis 40 according to FIG. 4 it has the shape of a slotted bell 42. Both configurations serve to secure the respective auditory ossicle prosthesis 30; 40 to a member of the auditory ossicle chain, for example to the anvil or to the stirrup.

Figure 5:
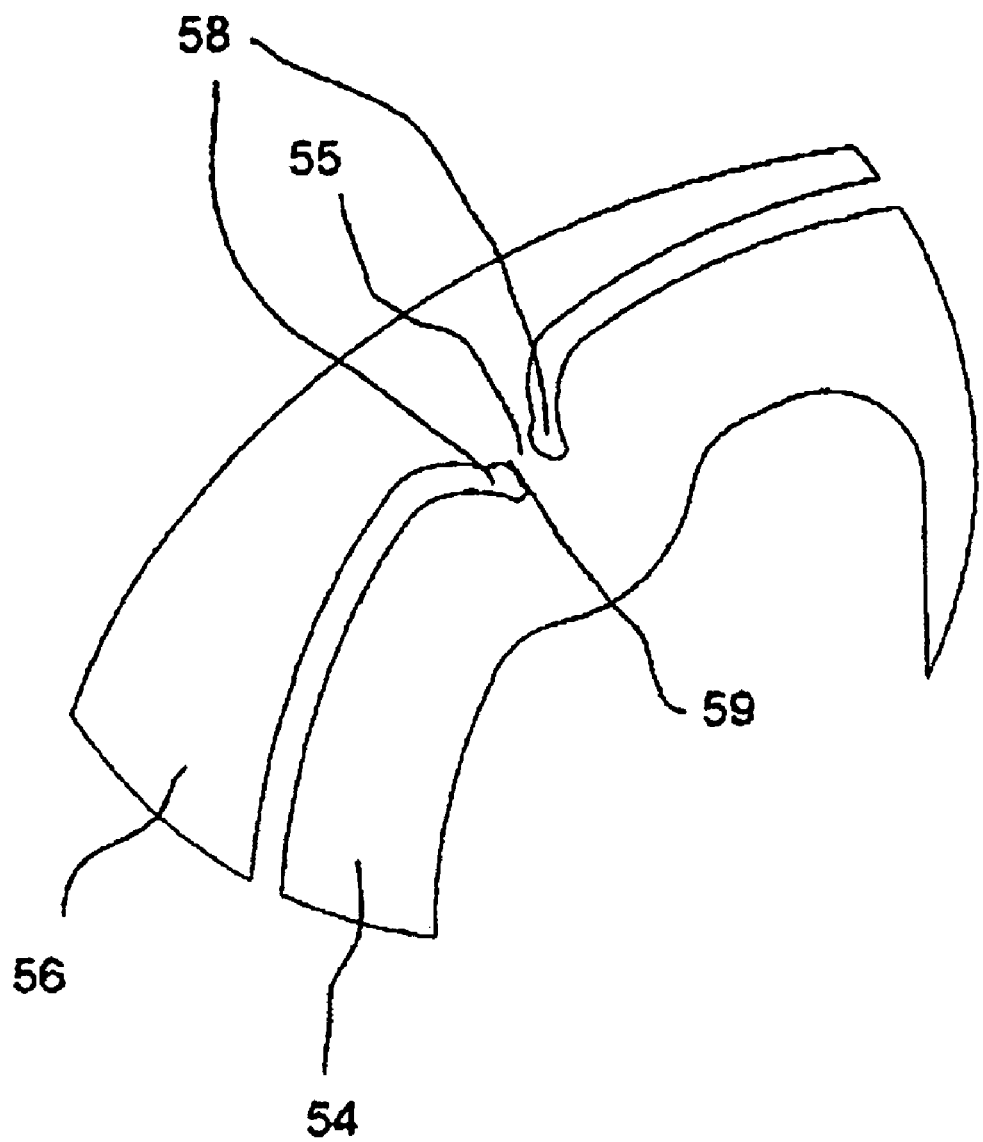
FIG. 5 shows a schematic illustration of a web element that is enclosed by a recess and has a predetermined break point.

As is indicated in all the figures of the drawing and as is shown in detail in the schematic view in FIG. 5, the web elements 15, 15', 15"; 25, 25'; 35, 35', 35"; 55 each open into a recess 58 of the central coupling area 14; 24; 34; 54 and/or of one of the radially outer portions 16, 16', 16"; 26, 26'; 36, 36', 36"; 56. The recess 58, in the plane of the plate of the plate-shaped first securing element 11; 21; 31, radially encloses the corresponding web element 55 to such an extent that the web element 55 extends along at least ¼, preferably at least ⅓, of its length within the recess 58. Moreover, the web elements 15, 15', 15"; 25, 25'; 35, 35', 35"; 55 each have a predetermined break point 59 with a minimum width of the respective web element in this area. The predetermined break point 59 is arranged in the plane of the plate of the plate-shaped first securing element 11; 21; 31 within the recess 58.

The weight distribution of the individual parts of the auditory ossicle prosthesis 10; 20; 30; 40 according to the invention can be calculated as a function of a desired, predefinable frequency response of the sound conduction in the middle ear, in such a way that individual tuning of the sound conduction properties is made possible.

In other embodiments of the auditory ossicle prosthesis according to the invention that are not specifically shown in the drawing, the central coupling areas and/or the web elements and/or the radial outer portions can also have other geometries in order to achieve the desired surface variability of the respective first securing element or the particularly desired strength properties. For example, the radially outer portions can also be designed with one or more interruptions or can be designed in a continuous ring shape, and they can have an undulating outer contour and/or protrusions or recesses in their azimuthal plane, for example for receiving the manubrium. Embodiments are also possible in which extension pieces are provided which, like jigsaw pieces, can be joined on from the side onto the outer edge of the plate-shaped first securing element in the plane of the plate.

The invention claimed is:

1. An auditory ossicle prosthesis which replaces or spans at least one member or parts of one member of an ossicular chain, the auditory ossicle prosthesis comprising: at one end, a substantially plate-shaped first securing element for bearing on a tympanic membrane or on a footplate of a stirrup, and, at its other end, a second securing element for mechanical connection to a member or parts of a member of the ossicular chain or to the inner ear, and also a connection element connecting the first and second securing elements to each other so as to conduct sound, and wherein the plate-shaped first securing element has a radially inner coupling area centrally arranged around an area centroid of the plate-shaped first securing element mechanically coupling the plate-shaped first securing element to the connection element, and also a plurality of web elements radially connecting the radially inner coupling area to at least one radially outer portion of the plate-shaped first securing element, wherein the web elements each have at least one predetermined break point located at a minimum width point of the respective web element, and wherein the web elements are of such a geometric configuration, and their material so chosen, that at least one of the web elements can be broken off from the plate-shaped first securing element at the predetermined break point and the at least one radially outer portion appended to the at least one of the web elements is also detached from the plate-shaped first securing element, such that an external diameter of the plate-shaped first securing element is reduced in this area.

2. The auditory ossicle prosthesis according to claim 1, wherein the plate-shaped first securing element has a thickness of between 0.01 mm and 0.5 mm and a minimum diameter of between 1.5 mm and 8 mm, and the web elements have a maximum width of between 0.01 mm and 0.2 mm.

3. The auditory ossicle prosthesis according to claim 1, wherein starting from the central coupling area, the web elements extend radially outward in a star shape, with a respective one of the at least one radial outer portion being appended to each of them, and in that a further radially outer portion is appended to each of these radially outer portions via further web elements.

4. The auditory ossicle prosthesis according to claim 1, wherein the at least one radially outer portion of the plate-shaped first securing element forms an outer ring area.

5. The auditory ossicle prosthesis according to claim 4, wherein the outer ring area, in a plane of the plate-shaped first securing element, has an undulating outer contour.

6. The auditory ossicle prosthesis according to claim 4, wherein the web elements have a maximum width b, and the radially outer ring area has a maximum width B, and that b<B.

7. The auditory ossicle prosthesis according to claim 1, wherein the web elements have a maximum width b, and the plate-shaped first securing element has a minimum diameter D, and in that b≦0.05.

8. The auditory ossicle prosthesis according to claim 1, wherein the web elements each open into a recess of the central coupling area and/or of one of the at least one radially outer portion.

9. The auditory ossicle prosthesis according to claim 8, wherein the recess, in a plane of a plate of the plate-shaped first securing element, radially encloses the corresponding web element to such an extent that the corresponding web element extends along at least ¼ of its length within the recess.

10. The auditory ossicle prosthesis according to claim 8, wherein the predetermined break point, in a plane of a plate of the plate-shaped first securing element, is arranged within the recess.

11. The auditory ossicle prosthesis according to claim 1, wherein at least parts of the auditory ossicle prosthesis are made of a material with a shape memory.

12. The auditory ossicle prosthesis according to claim 1, wherein a weight distribution of individual parts of the prosthesis is calculated as a function of a desired, predefinable frequency response of a sound conduction in a middle ear.

13. The auditory ossicle prosthesis according to claim 1, wherein at least one additional weight is secured on the auditory ossicle prosthesis or on a part of the auditory ossicle chain as a function of a desired, predefinable frequency response of a sound conduction in a middle ear.

14. The auditory ossicle prosthesis according to claim 1, wherein the prosthesis is connected to an active vibration part or an active hearing aid.

15. The auditory ossicle prosthesis according to claim 6, wherein 2b<B.

16. The auditory ossicle prosthesis according to claim 7, wherein b is about 0.03 D.

17. The auditory ossicle prosthesis according to claim 9, wherein the corresponding web element extends along at least ⅓ of its length within the recess.

18. The auditory ossicle prosthesis according to claim 1, wherein the second securing element is plate-shaped with breakable web elements and with at least one radially outer portion appended thereto, wherein the first securing element is designed to allow the auditory ossicle prosthesis to bear on the footplate of the stirrup, and the second securing element serves as a flat headplate for mechanical connection to the tympanic membrane.

19. The auditory ossicle prosthesis according to claim 4, wherein the outer ring area has at least one interruption.

20. The auditory ossicle prosthesis according to claim 4, wherein the outer ring area has an oval or circular shape.

21. The auditory ossicle prosthesis according to claim 4, wherein the outer ring area has a unilateral recess for receiving a manubrium.

22. The auditory ossicle prosthesis according to claim 4, wherein the outer ring area, in a plane of the plate-shaped first securing element, has a bulge extending radially outward.

* * * * *